US006562911B2

(12) United States Patent
Jing et al.

(10) Patent No.: US 6,562,911 B2
(45) Date of Patent: May 13, 2003

(54) FLUOROPOLYMER COMPOSITION WITH ORGANO-ONIUM AND BLOCKED OXALATE COMPOUNDS

(75) Inventors: Naiyong Jing, Woodbury, MN (US); Brant U. Kolb, Afton, MN (US); Robert E. Kolb, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/033,485

(22) Filed: Dec. 28, 2001

(65) Prior Publication Data

US 2002/0091282 A1 Jul. 11, 2002

Related U.S. Application Data

(62) Division of application No. 09/415,552, filed on Oct. 8, 1999, now Pat. No. 6,359,166.

(51) Int. Cl.$^7$ .......................... C08L 27/22; C08L 27/24
(52) U.S. Cl. ................... 525/326.3; 525/132; 525/146; 525/192; 525/194; 525/383; 525/384; 525/386; 525/326.4
(58) Field of Search ........................ 525/326.3, 326.4, 525/192, 194, 383, 384, 386, 132, 146

(56) References Cited

U.S. PATENT DOCUMENTS

| | | |
|---|---|---|
| 3,702,280 A | 11/1972 | Anderson |
| 3,876,654 A | 4/1975 | Pattison |
| 4,233,421 A | 11/1980 | Worm |
| 4,446,216 A | 5/1984 | Smith et al. |
| 4,882,390 A | 11/1989 | Grootaert et al. |
| 4,912,171 A | 3/1990 | Grootaert et al. |
| 5,086,123 A | 2/1992 | Guenthner et al. |
| 5,262,490 A | 11/1993 | Kolb et al. |
| 5,591,804 A | 1/1997 | Coggio et al. |
| 5,654,375 A | 8/1997 | Jing et al. |
| 5,728,773 A | 3/1998 | Jing et al. |
| 5,756,588 A | 5/1998 | Kolb et al. |
| 5,811,573 A | 9/1998 | Ishihira et al. |

FOREIGN PATENT DOCUMENTS

| | | |
|---|---|---|
| EP | 0 879 851 A1 | 11/1998 |
| WO | WO 98/08906 | 3/1998 |

OTHER PUBLICATIONS

W.M. Grootaert et al., Fluorocarbon Elastomers, 8 Kirk–Othmer Encyclopedia of Chemical Technology 990—1005 (4th ed. 1993).

Primary Examiner—D. R. Wilson
(74) Attorney, Agent, or Firm—Scott A Bardell

(57) ABSTRACT

In one aspect, the invention provides curable fluoropolymer compositions comprising fluoropolymer, onium, and alkyl or aryl oxalate-blocked compound as a crosslinking agent. In other aspects, the invention provides methods of making curable fluoropolymer compositions and provides alkyl or aryl oxalate-blocked compounds.

13 Claims, No Drawings

FLUOROPOLYMER COMPOSITION WITH ORGANO-ONIUM AND BLOCKED OXALATE COMPOUNDS

CROSS REFERENCE TO RELATED APPLICATION

This divisional application claims priority from U.S. application Ser. No. 09/415,552, filed Oct. 8, 1999 now U.S. Pat. No. 6,359,166, now allowed.

FIELD OF THE INVENTION

This invention relates to curing agents for fluoropolymers and to curable fluoropolymer compositions. In another aspect, the present invention relates to delayed curing fluoropolymer compositions.

BACKGROUND OF THE INVENTION

Fluorocarbon elastomers are synthetic elastomeric polymers with a high fluorine content—see, for example, W. M. Grootaert et al., Fluorinated Elastomers, 8 KIRK-OTHMER ENCYCLOPEDIA OF CHEMICAL TECHNOLOGY 990–1005 (4th ed. 1993). Fluorocarbon elastomers, particularly the copolymers of vinylidene fluoride with other ethylenically unsaturated halogenated monomers such as hexafluoropropene ($C_3F_6$), have become the polymers of choice for high temperature applications, such as seals, gaskets, and linings. These fluoropolymers exhibit favorable properties against the exposure to aggressive environments such as solvents, lubricants, and oxidizing or reducing agents. Additionally, these polymers can be compounded and cured to have high tensile strength, good tear resistance, and low compression set.

Presently used curing agents for fluoropolymers include aromatic polyhydroxy compounds, such as polyphenols, used in combination with certain vulcanization accelerators such as ammonium, phosphonium, or sulfonium compounds. U.S. Pat. Nos. 4,882,390 (Grootaert et al.); 4,912,171 (Grootaert et al.); and 5,086,123 (Guenthner et al.), for example, describe these compounds.

In accordance with conventional curing processes, desired amounts of compounding ingredients and other conventional adjuvants or ingredients are added to unvulcanized fluorocarbon elastomer stock and intimately admixed or compounded therewith by employing any of the usual rubber mixing devices such as Banbury mixers, roll mills, or other convenient mixing device. The components and adjuvants are distributed throughout the fluorocarbon gum during milling, during which period the temperature of the mixture typically will not rise above about 120° C. The curing process typically comprises either injecting (injection molding) the compounded mixture into a hot mold or pressing (compression molding) the compounded mixture in a mold, for example, a cavity or a transfer mold, followed subsequently by an oven-cure (post cure).

Many conventional fluoropolymer compositions tend toward "scorching" behavior, that is, the premature crosslinking or partial cure of the composition when exposed to elevated temperatures or conditions of high shear. This scorching behavior particularly is pronounced when the fluoropolymer is injection molded, wherein scorching is characterized by a premature cure initiation occurring prior to and during injection of the compounded composition into a mold. This can cause non-uniform curing of the fluoropolymer and results in poor physical properties. The point of cure initiation for injection-molded fluoropolymers may be defined as the time after which the compounded fluoropolymer is subjected to injection-molding conditions (that is, upon introduction into an injection barrel at a temperature of approximately 70–90° C. and/or while injecting the compound into the mold under high shear at temperatures between about 180° C. and 200° C.) when the curing compound begins to gel or harden. Such a change in physical properties, particularly the corresponding viscosity increase, can greatly reduce processing efficiency by hindering the ability to inject the compounded mixture into a mold. Scorching phenomena also produce high levels of waste product; because a cured fluoropolymer is very difficult to reprocess, any fluoropolymer that cures outside the mold cavity must usually be discarded.

Thus, there exists a need for fluoropolymer curing agents that provide a composition having improved scorch safety and end-use products having improved physical properties.

SUMMARY OF THE INVENTION

In one aspect, the present invention provides curable fluoropolymer compositions comprising the reaction product of: (a) fluorine-containing polymer or blend of fluorine-containing polymers each comprising interpolymerized units derived from one or more fluorine-containing ethylenically unsaturated monomers; (b) organo-onium compound; and (c) oxalate-blocked crosslinking agent.

In another aspect, the invention provides a method of curing a fluoropolymer comprising the steps of: (a) mixing organo-onium compound and oxalate-blocked compound into said fluoropolymer to form a curable fluoropolymer composition, said onium and oxalate-blocked compounds present in a sufficient amount to crosslink said fluoroelatomer to the desired degree; and (b) heating the curable fluoropolymer composition at a temperature of from about 180 to 210° C. for a sufficient time to crosslink said fluoropolymer.

In another embodiment, the invention provides a composition of matter comprising an oxalate-blocked compound having the formula:

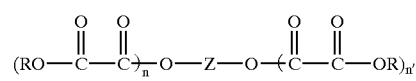

wherein

Z is an aryl or polyaryl group;

R is an aryl group or an alkyl group; and n and n' each is independently selected as 0 or 1 with the proviso that when either n or n' is 0, its corresponding portion of the Z moiety is terminated by hydrogen (that is, its corresponding terminal portion is —Z—OH) or is terminated by a metal or nonmetal cation.

The combinations of an organo-onium compound and the oxalate curing agents of the present invention provide increased processing control in the curing of fluoropolymer compositions, and in the formation of articles derived therefrom, without adversely affecting the physical properties of those cured compositions and articles.

The use of oxalate-blocked crosslinking agent in accordance with the teachings of the invention, either alone or in combination with one or more other crosslinking agents, yields improved scorch safety of curable fluoropolymers by providing a retarded cure at pre-molding temperatures below about 150° C. and a rapid cure at molding temperatures of about 180 to about 210° C. The ability significantly to retard this curing mechanism outside of the mold (where the temperature of the admixture typically do not exceed 150° C.) drastically reduces the probability of severe scorching behavior and consequently reduces attendant processing difficulties. For example, such ability allows for heating of the compound in a cold runner injection-molding process without scorching, thereby reducing the amount of waste generated while also reducing cycle times.

DETAILED DESCRIPTION OF THE INVENTION

Among the polymers that may be compounded in accordance with this invention are generally the fluoropolymers whose interpolymerized units are derived from one or more of the following fluoromonomers: vinylidene fluoride, vinyl fluoride, hexafluoropropene, chlorotrifluoroethylene, 2-chloropentafluoropropene, fluorinated vinyl ethers, fluorinated allyl ethers, tetrafluoroethylene, 1-hydropentafluoropropene, dichlorodifluoroethylene, trifluoroethylene, and mixtures thereof. Said fluoromonomers may also be copolymerized with other compounds such as with other cure-site monomers (for example, bromine-containing monomers or perfluorinated monomers such as perfluorobenzyl vinyl ether) or with non-fluorinated alpha-olefin co-monomers (for example, ethylene or propylene). Preferred fluoropolymers are copolymers of vinylidene fluoride and at least one terminally ethylenically-unsaturated fluoromonomer containing at least one fluorine atom substituent on each double-bonded carbon atom, each carbon atom of said fluoromonomer being substituted only with fluorine and optionally with chlorine, hydrogen, a lower fluoroalkyl radical, or a lower fluoroalkoxy radical.

Fluoropolymer copolymers according to the type described above are available commercially as copolymer gumstock under, for example, the "Fluorel" trademark by Dyneon LLC, Saint Paul, Minn. Suitable products of these lines include THV™ 200 and Fluorel™ FC-2230, FC-2145, FC-2178, and FC-2211. Other commercially available products include fluoropolymers sold under the "Viton" trademark.

The organo-onium compound which is admixed with the fluorine-containing polymer is capable of functioning as a vulcanization accelerator. As is known in the art, an organo-onium is the conjugate acid of a Lewis base (for example, phosphine, amine, ether, and sulfide) and can be formed by reacting said Lewis base with a suitable alkylating agent (for example, an alkyl halide or acyl halide) resulting in an expansion of the valence of the electron donating atom of the Lewis base and a positive charge on the organo-onium compound. Many of the organo-onium compounds useful in the present invention contain at least one heteroatom, that is, a non-carbon atom such as N, P, S, O, bonded to organic or inorganic moieties. One class of quaternary organo-onium compounds particularly useful in the present invention broadly comprises relatively positive and relatively negative ions wherein a phosphorus, arsenic, antimony or nitrogen generally comprises the central atom of the positive ion, and the negative ion may be an organic or inorganic anion (for example, halide, sulfate, acetate, phosphate, phosphonate, hydroxide, alkoxide, phenoxide, bisphenoxide, etc.).

Many of the organo-onium compounds useful in this invention are described and known in the art. See, for example, U.S. Pat. Nos. 4,233,421 (Worm); 4,912,171 (Grootaert et al.); 5,086,123 (Guenthner et al.); and 5,262,490 (Kolb et al.), all of whose descriptions are herein incorporated by reference. Representative examples include the following individually listed compounds and mixtures thereof:

triphenylbenzyl phosphonium chloride tributylallyl phosphonium chloride tributylbenzyl ammonium chloride tetrabutyl ammonium bromide triaryl sulfonium chloride 8-benzyl-1,8-diazabicyclo [5,4,0]-7-undecenium chloride benzyl tris(dimethylamino) phosphonium chloride benzyl(diethylamino)diphenylphosphonium chloride Another class of organo-oniums finding utility in the practice of this invention include acid-functional oniums that can represented by Formula I below.

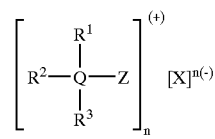

wherein:

Q is a nitrogen, phosphorus, arsenic, or antimony;

Z may be a substituted or unsubstituted, cyclic or acyclic alkyl group having from 4 to about 20 carbon atoms that is terminated with a group of the formula —COOA where A is a hydrogen atom or is a metal cation or Z is a group of the formula $CY_2$—COOR' where Y is a hydrogen or halogen atom, or is a substituted or unsubstituted alkyl or aryl group having from 1 to about 6 carbon atoms that may optionally contain one or more catenary heteroatoms and where R' is a hydrogen atom, a metal cation, an alkyl group, or is an acyclic anhydride, for example, a group of the formula —COR where R is an alkyl group or is a group that itself contains organo-onium (that is, giving a bis organo-onium); preferably, R' is hydrogen; Z may also be a substituted or unsubstituted, cyclic or acyclic alkyl group having from 4 to about 20 carbon atoms that is terminated with a group of the formula —COOA where A is a hydrogen atom or is a metal cation;

$R^1$, $R^2$, and $R^3$ are each independently an alkyl, aryl, alkenyl, or any combination thereof; each $R^1$, $R^2$, and $R^3$ can be substituted with chlorine, fluorine, bromine, cyano, —OR" or —COOR" where R" is a $C_1$ to $C_{20}$ alkyl, aryl, aralkyl, or alkenyl, and any pair of the $R^1$, $R^2$, and $R^3$ groups can be connected with each other and with Q to form a heterocyclic ring; one or more of the $R^1$, $R^2$, and $R^3$ groups may also be group of the formula Z where Z is as defined above;

X is an organic or inorganic anion (for example, halide, sulfate, acetate, phosphate, phosphonate, hydroxide, alkoxide, phenoxide, or bisphenoxide); and n is a number equal to the valence of the anion X.

Another class of useful organo-onium compounds include those having one or more pendent fluorinated alkyl groups. Generally, the most useful such fluorinated onium compounds are disclosed in U.S. Pat. No. 5,591,804 (Coggio et al.). Representative of this useful class of onium compounds are the following:

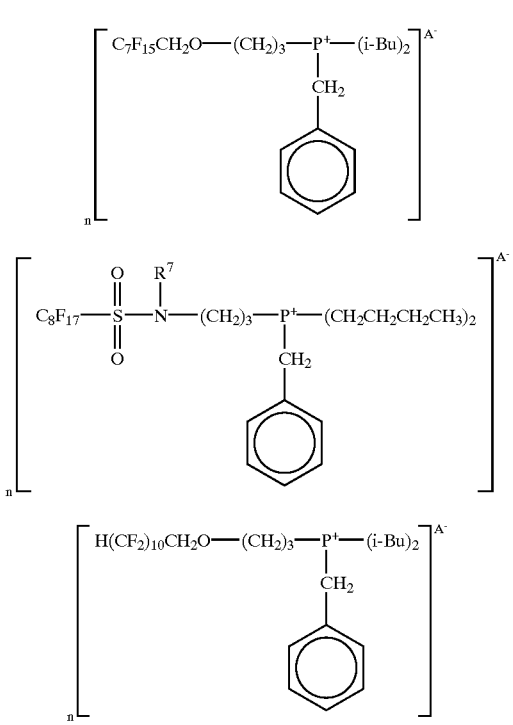

Useful oxalate blocked compounds used as crosslinking agents in accordance with the present invention have the formula:

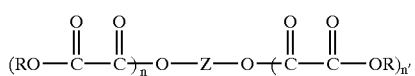

wherein Z is an arylene or polyarylene group, and is preferably a polyphenylene group of the formula:

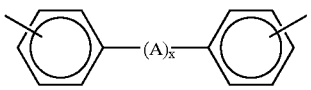

wherein

A is a difunctional aliphatic, cycloaliphatic, or aromatic radical of 1 to 13 carbon atoms, or a thio, oxy, carbonyl, sulfonyl, or sulfonyl radical, A is optionally substituted with at least one chlorine or fluorine atom, x is 0 or 1;

R is an aryl group or an alkyl group; and n and n' each is independently selected as 0 or 1 with the proviso that when either n or n' is 0, its corresponding portion of the Z moiety is terminated by hydrogen (that is, its corresponding terminal portion is —Z—OH) or is terminated by a metal or nonmetal cation.

Preferably, A is a difunctional aliphatic radical or a difunctional perfluoroaliphatic radical.

Oxalate-blocked compounds useful in the formulations described above wherein each depicted —R group is independently selected as a substituted or unsubstituted aryl group such as those aryl substituent groups according to Formula VI below.

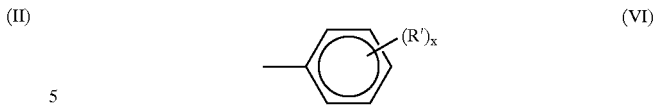

where x is a number between 1 and 4 inclusive and where R' is hydrogen, a halogen atom, or is an acyl, aryl, polyaryl (fused to or separated from the aromatic ring) or alkyl radical substituent (or any combination thereof), the latter three of which may be fluorinated but are preferably non-fluorinated and may be straight-chained, branched, cyclic. The —R' group may optionally contain one or more catenary heteroatoms, that is, a non-carbon atom such as nitrogen or oxygen. It will be understood from the above formula that the constituent —R' group can be attached in any position in the ring relative to the bond attaching it to the oxalate group depicted in Formula V.

Useful alkyl groups (R in the above formula) include alkyl groups having from 2 to 20 carbon atoms. The alkyl groups may be cyclic or acyclic, linear or branched, fluorinated or non-fluorinated, may be un-substituted or may be substituted with an aryl or one or more functional groups, and may contain one or more catenary heteroatoms. Preferred alkyl and substituted alkyl groups include ethyl, propyl, and isopropyl.

It will be understood that the oxalate-blocked compounds may be oligomerized oxalates. Oligomeric oxalates, so formed, are also useful in the practice of the invention and are considered within the scope thereof. It will be further understood that the above-depicted oxalate-blocked crosslinking agents may have only one oxalate substituent and where more than one oxalate substituent is present, that substituent may be the same or may be different in structure than the other substituent or substituents present. It will also be understood that the compositions of the invention may contain one or more oxalate blocked compounds or may contain a mixture of one or more oxalate-blocked compounds and one or more other crosslinking agents.

One type of conventional crosslinking agent for a fluorocarbon elastomer gum which may be used in combination with an oxalate-blocked crosslinking agent of the invention is a polyhydroxy compound. The polyhydroxy compound may be used in its free or non-salt form or as the anionic portion of the chosen organo-onium accelerator. The crosslinking agent may be any of those polyhydroxy compounds known in the art to function as a crosslinking agent or co-curative for fluoropolymers, such as those polyhydroxy compounds disclosed in U.S. Pat. Nos. 3,876,654 (Pattison) and 4,233,421 (Worm). Representative aromatic polyhydroxy compounds include any one of the following: di-, tri-, and tetrahydroxybenzenes, naphthalenes, and anthracenes, and bisphenols of the following formula:

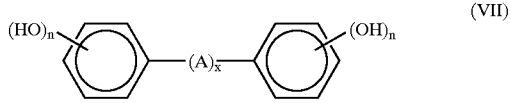

wherein A is a difunctional aliphatic, cycloaliphatic, or aromatic radical of 1 to 13 carbon atoms, or a thio, oxy, carbonyl, sulfonyl, or sulfonyl radical, A is optionally substituted with at least one chlorine or fluorine atom, x is 0 or 1, n is 1 or 2, and any aromatic ring of the polyhydroxy compound is optionally substituted with at least one atom of chlorine, fluorine, bromine, or with a carboxyl or an acyl radical (for example, —COR where R is H or a $C_1$ to $C_8$ alkyl, aryl, or cycloalkyl group) or alkyl radical with, for example, 1 to 8 carbon atoms. It will be understood from the above bisphenol formula that the —OH groups can be attached in any position (other than number one) in either ring. Blends of two or more of these compounds are also used.

One of the most useful and commonly employed aromatic polyphenols of the above formula is 4,4'-hexafluoroisopropylidenyl bisphenol, known more commonly as bisphenol AF. The compounds 4,4'-dihydroxydiphenyl sulfone (also known as bisphenol S) and 4,4'-isopropylidenyl bisphenol (also known as bisphenol A) are also widely used in practice.

Other classes of crosslinking agents that may be used in the compositions of the invention are the carbonate-blocked compounds described in U.S. Pat. No. 5,728,773, the description of which is incorporated by reference herein, and the monohydroxy functional phenol compounds described in U.S. Pat. No. 5,756,588, the description of which is incorporated by reference.

Fluoroaliphatic sulfonamides can also be added to the compositions of the invention, including those of the formula $R_f SO_2 NHR''$, where R'' is an alkyl radical having, for example, from 1 to 20 carbon atoms, preferably from 1 to 12 carbon atoms, $R_f$ is a fluoroaliphatic radical such as a perfluoroalkyl, for example, $C_n F_{2n+1}$ where n is 1 to 20, or perfluorocycloalkyl, for example, $C_n F_{2n-1}$ where n is 3 to 20, such compounds being described, for example, in U.S. Pat. No. 5,086,123 (Guenther et al.). The fluoroaliphatic sulfonamide is preferably a perfluoroalkylsulfonamide and may be added as a separate compound, or as the anion of the organo-onium compound.

Fillers can be mixed with the fluoropolymer gum to improve molding characteristics and other properties. When a filler is employed, it can be added to the vulcanization recipe in amounts of up to about 100 parts per hundred parts by weight of gum, preferably between about 15 to 50 parts per hundred parts by weight of the gum. Examples of fillers which may be used are reinforcing thermal or furnace grade carbon blacks or non-black pigments of relatively low reinforcement characteristics such as clays and barytes.

The cure accelerators and crosslinking agent or agents can be added to the uncured polymer gum in the form of finely divided solids or as solutions in alcohol or ketone solvents by mixing the materials into the polymer gum stock. Thus mixed, the gum stock can generally be stored at room temperature for extended periods of time.

Prior to curing, an acid acceptor is mixed into the gum stock, after which storage life of the stock is more limited. Acid acceptors can be inorganic or blends of inorganic and organic. Examples of inorganic acceptors include magnesium oxide, lead oxide, calcium oxide, calcium hydroxide, dibasic lead phosphite, zinc oxide, barium carbonate, strontium hydroxide, calcium carbonate, etc. Organic acceptors include epoxies, sodium stearate, and magnesium oxalate. The preferred acid acceptors are magnesium oxide and calcium hydroxide. The acid acceptors can be used singly or in combination, and preferably are used in amounts ranging from about 2 to 25 parts per 100 parts by weight of the polymer gum stock. All of the components of the curing system may be admixed prior to their incorporation into the polymer gum stock without departing from the scope of the invention.

The relative amounts of the crosslinking agent or agents (that is, the chosen total amount of aryl, alkyl, or allyl oxalate along with conventional crosslinking agents, if any) and onium salt are present in the composition in such amounts as to provide the desired cure and/or mold release of the composition when mixed with acid acceptor. Representative proportions of components of the curing system are as follows:

| Acid acceptor: | 0.5 to 40 phr |
| Onium salt: | 0.2 to 5 mmhr |
| Crosslinker: | 0.3 to 12 mmhr |

All amounts are given in parts per 100 parts polymer gum stock (abbreviated "phr") or in millimoles per hundred parts polymer gum stock (abbreviated "mmhr"). It will be understood that these proportions are general ranges; the particular amount for each particular cure time and temperature will be apparent to one of ordinary skill in the art.

In accordance with this invention, the desired amounts of compounding ingredients and other conventional adjuvants or ingredients are added to the unvulcanized fluorocarbon gum stock and intimately admixed or compounded therewith by employing any of the usual rubber mixing devices such as internal mixers, (for example, Banbury mixers), roll mills, or any other convenient mixing device. For best results, the temperature of the mixture on the mill typically should not rise above about 120° C. During milling, it is preferable to distribute the components and adjuvants uniformly throughout the gum for effective cure.

The mixture is then processed and shaped, for example, by extrusion (for example, in the shape of a hose or hose lining) or molding (for example, in the form of an O-ring seal). The shaped article can then be heated to cure the gum composition and form a cured elastomer article.

Pressing of the compounded mixture (that is, press cure) is usually conducted at a temperature between about 95° C. and about 230° C., preferably between about 150° C. and about 205° C., for a period of from 1 minute to 15 hours, typically from 5 minutes to 30 minutes. A pressure of between about 700 kPa and about 20,600 kPa is usually imposed on the compounded mixture in the mold. The molds first may be coated with a release agent and prebaked. The molded vulcanizate is then usually post-cured (for example, oven-cured) at a temperature usually between about 150° C. and about 275° C., typically at about 232° C., for a period of from about 2 hours to 50 hours or more depending on the cross-sectional thickness of the article. For thick sections, the temperature during the post cure is usually raised gradually from the lower limit of the range to the desired maximum temperature. The maximum temperature used is preferably about 260° C., and is held at this value for about 4 hours or more. The compositions of this invention can be used to form seals, O-rings, gaskets, etc.

EXAMPLES

All of the reagents used in the examples below are available from Aldrich Chemical Company Inc, Milwaukee, Wis., unless otherwise indicated.

Test Methods

In the following examples, indicated results were obtained using the following test methods:

Cure Rheology Tests were run on uncured, compounded admixture using a Monsanto Moving Die Rheometer (MDR) Model 2000 in accordance with ASTM D 5289-93a at 150° C., 177° C., and 200° C., no preheat, for the indicated time (60, 12, or 6 minutes), and a 0.5° arc. Minimum torque ($M_L$) and Maximum torque ($M_H$), that is, highest torque attained during specified period of time when no plateau or maximum torque is obtained, were reported. Also reported were TS2 (time for torque to increase 2 units above $M_L$, T50 [time for torque to reach $M_L+0.5(M_H-M_L)$], and T90 [time for torque to reach $M_L+0.9(M_H-M_L)$]).

Tensile Strength at Break, Elongation at Break, and Modulus at 100 percent Elongation were determined using ASTM D 412-92$^\epsilon$ on samples cut from the press-cure or post-cure sheet with ASTM Die D. Units reported in Mega Pascals (MPa).

Compression set determined by ASTM 395-89 Method B with 0.139 inch (3.5 mm) After post-curing, the O-rings were compressed for 70 hours at 200° C. Results are reported as percent.

The following oxalate-blocked bisphenols were used as crosslinking agents in the following examples.

Example 1

Synthesis of Oxalate A
Bisphenol-AF bis(Ethyl Oxalate)

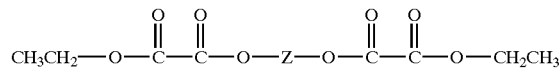

Z=Bisphenol AF radical

A glass round bottom flask was assembled with a stirring bar, a refluxing condenser, and a thermometer. The flask was charged with 17 grams of 4,4'-hexafluoroisopropylidene-diphenol (bisphenol AF), 100 mL of methylene chloride, and 14 mL of triethylamine. The reaction solution was stirred at room temperature until the bisphenol-AF was dissolved. Fifteen grams of ethyl oxaly chloride was slowly added to the reaction mixture under stirring. Some white precipitate appeared in the solution, which was believed to be hydrochloric ammonia salt. The solution was stirred for 2–3 hours. The white solid was filtered and then washed with a small amount of methylene chloride. The filterate and the washed methylene chloride were combined and washed with cold water (4×150 mL) and 150 mL 0.3 N HCl and the washed filtrate was dried over $MgSO_4$ overnight. The $MgSO_4$ salt was filtered and washed with about 30 mL of methylene chloride. The solvent was removed on a rotary evaporator and the resulting white solid was further dried under vacuum to give 24.9 grams (92 percent yield) of the expected product. $^1$HNMR (400 MHz, $CDCl_3$), 7.45 (d, J=36 Hz, 4 H), 7.26 (d, J=36 Hz, 4 H), 4.43 (q, J=18 Hz, 4 H), 1.42 (t, J=18 Hz, 6 H), $^{19}$FNMR (376 Hz, $CDCl_3$), −64.4 (s, 6 F).

Synthesis of Bisphenol AF Bisoxalyl Chloride Adduct (Bisphenol AF Bisoxalyl Chloride)

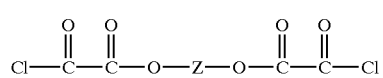

Z=Bisphenol AF Radical

Bisphenol AF (50 grams, 148.8 mmole) and dichloroethane (625 grams) were charged to a flask fitted with a fractionation column and a still head attached to a NaOH bubbler. Nitrogen was bubbled through the reaction vessel. To this was added oxalyl chloride (145 grams, 1.141 mole). The mixture was heated to reflux (~90° C.) and all components were dissolved. The reaction was run at this temperature for 6 hours with the $N_2$ sparge to remove the HCl. When the reaction was completed, the N2 sparge was stopped and the solvent and residual oxalyl chloride were distilled off. This resulted in an orange liquid which was further stripped under vacuum at which time the material crystallized. The product was isolated 76.9 (100 percent yield). $^1$HNMR (500 MHz, $CDCl_3$), 7.50 (d, J=34 Hz, 4 H), 7.32 ppm (d, J=36 Hz, 4 H); $^{19}$F (470 MHz, $CDCl_3$), −64.324 ppm (S, 6 F).

Example 2

Synthesis of Oxalate B

Bisphenol-AF bis(Propyl Oxalate)

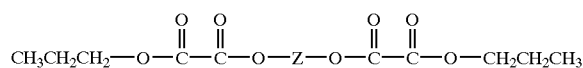

Z=Bisphenol AF Radical

A glass round bottom flask was assembled with a stirring bar, a refluxing condenser and a thermometer. Into the flask was placed Bisphenol AF bisoxalyl chloride (10.0 grams, 19.3 mmol), 80 mL of methylene chloride, the solution was cooled to −35° C. with a dry ice/isopropanol/water bath. To the solution was slowly added dry n-propanol (2.4 grams, 40 mmol) in 25 mL $CH_2Cl_2$. After the completion of the addition, the reaction was further carried out for 1 hour at −35° C. and for 2 hours at room temperature. Then the reaction solution was concentrated to give a viscous liquid by distillation under reduced pressure and the viscous liquid was solidified to give 10.9 grams of the expected product in 100 percent yield. $^1$HNMR (500 MHz, $CDCl_3$), 7.40 (d, J=36 Hz, 4 H), 7.19 (d, J=36 Hz), 4.23 (t, J=18 Hz, 4 H), 1.67 (6 splits, J=18 Hz, 4 H), 0.8 ppm (t, J=18 Hz, 6 H), FNMR (470 MHz, $CDCl_3$), −64.35 ppm (s, 6 F).

Example 3

Synthesis of Oxalate C

Synthesis of Bisphenol AF Oxalate Oligomers

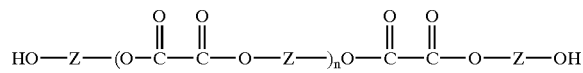

Z=Bisphenol AF Radical

Bisphenol AF (70 grams, 208 mmole) and dichloroethane (509 grams) were charged to the reaction flask described above. To the solution was added oxalyl chloride (32.79 grams, 258.33 mmole) in 50 grams of dichloroethane. The reaction was run with $N_2$ sparge at ~80° C. for approximately 7 hours. Then more oxalyl chloride (1.35 grams, 10.82 mmole) was added and reacted for an additional 2.5 hours. The reaction was run further and eventually white solids precipitated out of the solution. The solvent was stripped off on a rotary evaporator, washed with heptane and redried. The product was a hard white solid. $^1$HNMR (400 MHz, d-acetone), 7.50–7.30 (m, 50 H), 7.10 (m, 1.5 H), 6.80 (m, 1.5 H), 6.16 ppm (s, 1 H), $^{19}$FNMR (376 MHz, d-acetone), −63.44 (s, 5.2 F), −63.6 ppm (s, 0.8 F).

Example 4

Synthesis of Oxalate D

Bisphenol-AF bis(4-chlorophenyl Oxalate)

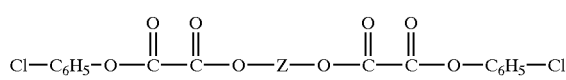

Z=Bisphenol AF Radical

By the method described above, Bisphenol AF bisoxalyl chloride (10.0 grams, 19.3 mmol) in 80 mL of methylene chloride was reacted with 4-chlorophenol (5.0 grams, 38 mmol) in 20 mL of methylene chloride at −20° C. After addition, the reaction solution was heated to refluxing overnight. Then, the reaction mixture was concentrated to give 13.3 grams of the desired product (100 percent yield). $^1$HNMR (400 MHz, CDCl$_3$), 7.42(d, J=36 Hz, 4H), 7.26 (d, J=36 Hz, 4 H), 7.22 (d, J=36 Hz, 4 H), 7.16 ppm (d, J=36 Hz, 4 H), FNMR (376 MHz, CDCl$_3$), −64.3 ppm (s, 6 F).

Example 5

Synthesis of Oxalate E

Bisphenol-AF bis(Phenyl Oxalate)

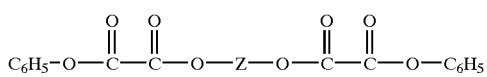

Z=Bisphenol AF Radical

By the method described above, Bisphenol AF bisoxalyl chloride (4.4 grams, 8.5 mmol) in 60 mL of methylene chloride was reacted with phenol (1.6 grams, 17.0 mmol) in 40 mL of methylene chloride at −40° C. After addition, the reaction solution was allowed to slightly reflux under nitrogen atmosphere overnight. The reaction solution was concentrated to give 5.4 grams desired product in 100 percent. $^1$HNMR (500 MHz, CDCl$_3$), 7.43 (d, J=36 Hz, 4 H), 7.39 (d, J=36 Hz, 4 H), 7.23 (m, 6 H), 7.20 ppm (d, J=36 Hz, 4 H), FNMR (470 MHz, CDCl$_3$), −64.33 ppm (s, 6 F).

Example 6

Synthesis of Oxalate F

Bisphenol-AF bis(Isopropyl Oxalate)

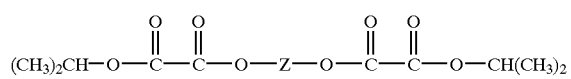

Z=Bisphenol AF Radical

By the method described above, Bisphenol AF bisoxalyl chloride (10.0 grams, 19.3 mmol) in 80 ml methylene chloride was reacted with a methylene chloride solution containing pre-dried isopropanol (2.4 grams, 40 mmol) to give the desired product 10.2 grams (94 percent) $^1$HNMR (400 MHz, CDCl$_3$), 7.38 (d, J=36 Hz, 4 H), 7.18 (d, J=36 Hz, 4H), 5.18 (7 splits, J=28 Hz, 2 H), 1.27 (d, J=28 Hz, 12 H), FNMR (376 MHz, CDCl$_3$), −64.37 ppm (s, 6 F).

Example 7

Synthesis of Oxalate G

Bisphenol-AF Bis(Octyl Oxalate)

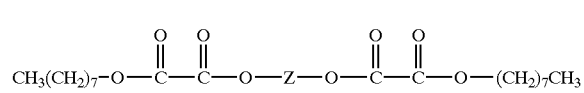

Z=Bisphenol AF Radical

Bisphenol AF bisoxalyl chloride (10.2 grams, 19.72 mmole) was dissolved in dichloroethane (23 grams). n-Octanol (5.14 grams, 39.53 mmole) was mixed with dichloroethane (40 grams). The alcohol solution was added slowly to the dichloroethane with stirring and cooling. The temperature was maintained at 10–15° C. for 2 hours. The reaction was allowed to proceed at room temperature overnight. The product was obtained by rotary evaporation and further under vacuum to give 13.8 grams (100 percent yield) of a light straw colored viscous liquid. $^1$HNMR (400 MHz, CDCl$_3$), 7.45 (d, J=36 Hz, 4 H), 7.25 (d, J =36 Hz, 4 H), 4.38 (t,J=18 Hz, 4 H), 1.8 (quintet, J=18 Hz, 4 H), 1.5–1.2 (m, 20 H), 0.9 ppm (t, J=18 Hz, 6 H), $^{19}$FNMR (376 MHz, CDCl$_3$) −64.42 ppm (s, 6 F).

The following onium catalysts were used in the examples below: Onium A is tributyl(2-methoxy)propylphosphonium chloride. Onium B is carboxylethyltributylphosphonium chloride.

Gum Type

Commercially available fluoropolymer gums were compounded with the above prepared compounds and various other ingredients and cured. The cure rheology and physical properties of the cured composition were then determined. Gum A was a copolymer which, except as otherwise indicated, has a Mooney Viscosity of 38 and nominal weight percents of interpolymerized units derived from 60 weight percent vinylidene fluoride and 40 weight percent hexafluoropropene. Gum B was a terpolymer having nominal weight percents of interpolymerized units derived from 44.5 weight percent vinylidene fluoride, 31.2 weight percent hexafluoropropene, and 24.3 weight percent tetrafluoroethylene and had a nominal Mooney Viscosity of 75. Some additives, such as curatives for example, are listed in quantities of millimoles per hundred parts of gum (mmhr). Other additives are listed in grams. Percentages are in weight percent unless otherwise specified.

Table 1 shows the composition of Examples 8–16. A series (Examples 8–14) of oxalate-blocked bisphenol AF derivatives were compounded in equal molar amounts of Gum A. Comparative Example 1 utilizes an unblocked bisphenol AF as a control. Example 15 and Comparative Example 2 show the effect of using different onium catalysts.

Rheology data in Table 2 show the cure kinetics for the compositions containing oxalate blocked compounds in comparison with those containing unblocked bisphenol compounds. The data show that the oxalate-blocked compounds delay the cure of the fluoropolymer compositions at lower temperatures and then allow the compositions to cure at higher temperatures.

Comparative Example 1 shows the kinetics at 150° C. of a composition using bisphenol AF as the crosslinking agent. The cure is essentially complete after 3.2 minutes (T90, Comparative Example 1). In contrast, the oxalate-blocked compounds (Examples 8–14) show that the cure time of the fluoropolymer composition can be extended out to 22–58 minutes depending on the specific oxalate-blocked compound used. The Maximum Torque data show that the oxalate compounds provide comparable curing of the composition as compared to the compositions containing bisphenol AF control. The rheology data show that a full curing of the compositions of the invention can be obtained at in 2–4 minutes at 200° C.

Examples 15 and 16 and Comparative Examples 2 and 3 show that similar results to those described above can be obtained using a different catalyst and different fluoropolymer gum.

Table 3 shows the physical properties for the Examples in Table 1.

TABLE 1

| | Comp. Ex. 1 | Ex. 8 | Ex. 9 | Ex. 10 | Ex. 11 | Ex. 12 | Ex. 13 | Ex. 14 | Comp. Ex. 2 | Ex. 15 | Comp. Ex. 3 | Ex. 16 |
|---|---|---|---|---|---|---|---|---|---|---|---|---|
| Gum A (g) | 100 | 100 | 100 | 100 | 100 | 100 | 100 | 100 | 100 | 100 | | |
| Gum B (g) | | | | | | | | | | | 100 | 100 |
| Ca(OH)$_2$ (g) | 6 | 6 | 6 | 6 | 6 | 6 | 6 | 6 | 6 | 6 | 6 | 6 |
| MgO (g) | 3 | 3 | 3 | 3 | 3 | 3 | 3 | 3 | 3 | 3 | 3 | 3 |
| Carbon Black (g) | 30 | 30 | 30 | 30 | 30 | 30 | 30 | 30 | 30 | 30 | 30 | 30 |
| Onium A (mmhr) | 1.5 | 1.5 | 1.5 | 1.5 | 1.5 | 1.5 | 1.5 | 1.5 | | | | |
| Onium B (mmhr) | | | | | | | | | 1.5 | 1.5 | 1.5 | 1.5 |
| Bisphenol AF (mmhr) | 6.0 | | | | | | | | 6.0 | | 6.0 | |
| Oxalate A (mmhr) | | 6.6 | | | | | | | | | | |
| Oxalate B (mmhr) | | | 6.0 | | | | | | | 6.0 | | 6.0 |
| Oxalate C (mmhr) | | | | 6.2 | | | | | | | | |
| Oxalate D (mmhr) | | | | | 6.0 | | | | | | | |
| Oxalate E (mmhr) | | | | | | 6.0 | | | | | | |
| Oxalate F (mmhr) | | | | | | | 6.0 | | | | | |
| Oxalate G (mmhr) | | | | | | | | 6.0 | | | | |

TABLE 3

| Sample | Comp. Ex. 1 | Ex. 8 | Ex. 9 | Ex. 10 | Ex. 11 | Ex. 12 | Ex. 13 | Ex. 14 | Comp. Ex. 2 | Ex. 15 | Comp. Ex. 3 | Ex. 16 |
|---|---|---|---|---|---|---|---|---|---|---|---|---|
| Tensile, MPa | 13.2 | 13.2 | 13.4 | 13.5 | 11.9 | 12.6 | 13.4 | 13.1 | 13.4 | 13.8 | 13.8 | 15.4 |
| Elongation, percent | 134 | 125 | 170 | 183 | 167 | 154 | 171 | 140 | 160 | 190 | 195 | 227 |
| Modulus, MPa | 8.1 | 10.2 | 6.6 | 6.4 | 6.1 | 7.3 | 6.5 | 8.4 | 7.5 | 5.2 | 6.5 | 5.4 |
| Shore A | 74 | 83 | 76 | 76 | 78 | 78 | 75 | 79 | 77 | 72 | 76 | 73 |
| Compression Set, percent | 22.8 | 17.9 | 18.0 | 23.7 | 30.5 | 29.4 | 21.1 | 30.6 | 23.2 | 22.8 | 22.3 | 18.6 |

Press cured 15 minutes at 177° C. and post cured 16 hours at 232° C.

Table 4 shows the compositions of Examples 17–20. These experiments demonstrate the effect of changing the onium salt to oxalate-blocked compound ratio for the ethyl oxalate-blocked bisphenol. The rheology data in Table 5 show that the oxalate-blocked compound will delay the cure of the composition at a temperature of 150° C. but provide rapid cure of the composition at a temperature of 200° C.

TABLE 4

| | Ex. 17 | Ex. 18 | Ex. 19 | Ex. 20 |
|---|---|---|---|---|
| Gum A (g) | 100 | 100 | 100 | 100 |
| Ca(OH)$_2$ (g) | 6 | 6 | 6 | 6 |
| MgO (g) | 3 | 3 | 3 | 3 |
| Carbon Black (g) | 30 | 30 | 30 | 30 |
| Onium A (mmhr) | — | — | — | 1.5 |
| Onium B (mmhr) | 1.20 | 1.80 | 2.16 | — |
| Oxalate A (mmhr) | 6.25 | 6.25 | 6.25 | 6.25 |

Table 5 show the rheology data for the samples described in Table 4.

TABLE 5

| | Ex. 17 | Ex. 18 | Ex. 19 | Ex. 20 |
|---|---|---|---|---|
| Cure Temp. 150° C., 60 minutes | | | | |
| Minimum Torque (in-lb) (J) | — | — | 1.11 (0.125) | 1.15 (0.130) |
| Maximum Torque, (in-lb) (J) | — | — | 25.04 (2.82) | 22.87 (2.58) |
| TS$_2$ (minutes) | — | — | 30.05 | 35.04 |
| T50 (minutes) | — | — | 36.46 | 42.69 |

TABLE 5-continued

| | Ex. 17 | Ex. 18 | Ex. 19 | Ex. 20 |
|---|---|---|---|---|
| T90 (minutes) | — | — | 51.89 | 55.09 |
| MDR 177° C., 12 minutes | | | | |
| Minimum Torque (in-lb) (J) | — | — | 0.48 (0.054) | 1.15 (0.130) |
| Maximum Torque (in-lb) (J) | — | — | 24.22 (2.73) | 24.09 (2.72) |
| TS$_2$ (minutes) | — | — | 5.84 | 5.4 |
| T50 (minutes) | — | — | 7.44 | 7.12 |
| T90 (minutes) | — | — | 9.64 | 9.73 |
| MDR 200° C., 6 minutes | | | | |
| Minimum Torque (in-lb) (J) | 0.31 (0.035) | 0.31 (0.035) | 0.30 (0.034) | 0.35 (0.040) |
| Maximum Torque (in-lb) (J) | 21.33 (2.41) | 23.7 (2.67) | 23.76 (2.68) | 23.34 (2.63) |
| TS$_2$ (minutes) | 7.81 | 2.67 | 1.99 | 1.70 |

TABLE 5-continued

|  | Ex. 17 | Ex. 18 | Ex. 19 | Ex. 20 |
|---|---|---|---|---|
| T50 (minutes) | 10.47 | 3.59 | 2.65 | 2.33 |
| T90 (minutes) | 15.31 | 5.43 | 4.04 | 3.45 |

Table 6 gives the mechanical properties for Example 20 and Comparative Example 4.

TABLE 6

| Examples | Ex. 20 | Comp. Ex. 4 |
|---|---|---|
| Tensile, psi (Mpa) | 1919 (13.22) | 1960 (13.50) |
| Elongation percent | 125 | 180 |
| Modulus, psi (Mpa) | 1478 (10.2) | 1000 (6.88) |
| Compression Set, percent | 17 | 16 |

Synthesis of Bis-Phenol A Dioxalyl Chloride Derivative

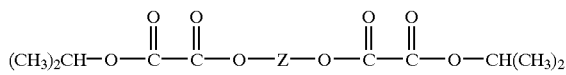

Z=bisphenol A radical

The reaction was performed under the conditions described above for the preparation of bisphenol AF bisoxalyl chloride Adduct (Bisphenol AF bisoxalyl chloride).

Bisphenol A (40.2 grams, 176.09 mmole) and dichloroethane (627 grams) were charged to a reaction flask and oxalyl chloride (147.5 grams, 1,162 mmole) was added. The reaction was heated to reflux (~100–110° C.). The reaction mixture was purged with nitrogen and allowed to react for 3 hours 45 minutes at which time the reaction looks complete by NMR analysis. At this time, the solvent and excess oxalyl chloride was removed via distillation. Solvent was further removed using a rotary evaporator to obtain 70.05 grams (104 percent yield) of an orange crystalline solid. $^1$HNMR (400 MHz, CDCl$_3$), 7.3 (d, J=50 Hz, 4 H), 7.15 (d, J=50 Hz, 4 H), 1.7 (s, 6 H).

Example 21

Synthesis of Oxalate H
Bisphenol-A bis(Isopropyl Oxalate)

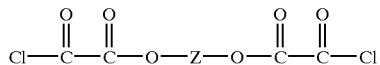

Z=bisphenol A radical

As described above, bisphenol-A bisoxalyl chloride (12.0 grams, 29.4 mmol) in 80 ml methylene chloride was reacted with 15 ml methylene chloride solution containing pre-dried isopropanol (3.6 grams, 60 mmol) to give the desired product 13.3 grams (99 percent) $^1$HNMR (400 MHz, CDCl$_3$), 7.19 (d, J=36 Hz, 4 H), 7.02 (d, J=36 Hz, 4 H), 5.18 (7 splits, J=28 Hz, 2 H), 1.34 (d, J=28 Hz, 12 H).

Example 22

Synthesis of Oxalate I
Bisphenol-A bis(n-propyl Oxalate)

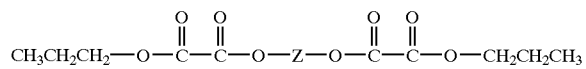

Z=bisphenol A radical

As described above, bisphenol-A bisoxalyl chloride (12.0 grams, 29.4 mmol) in 80 mL methylene chloride was reacted with 15 mL methylene chloride solution containing pre-dried n-propanol (3.6 grams, 60 mmol) to give the desired product 13.1 grams (98 percent) $^1$HNMR (400 MHz, CDCl$_3$), 7.22 (d, J=36 Hz, 4 H), 7.08 (d, J=36 Hz, 4 H), 4.32 (t, J=28 Hz, 4 H), 1.80(6 splits, J=28 Hz, 4 H) 1.0 (t, J=28 Hz, 6 H).

Example 23

Synthesis of Oxalate J
Bisphenol-A bis(Phenyl Oxalate)

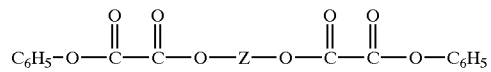

Z=bisphenol A radical

As described above, bisphenol-A bisoxalyl chloride (12.5 grams, 30.6 mmol) in 80 mL of methylene chloride was reacted with 20 mL methylene chloride solution containing phenol (5.3 grams, 63.0 mmol) to give the desired product 15.3 grams (99 percent) $^1$HNMR (400 MHz, CDCl$_3$), 7.39–7.12 (m, 18 H).

Table 7 shows the compositions of Examples 24–26. Table 8 shows the rheology data for Examples 24–26 and Table 9 shows the physical data for Examples 24–26.

TABLE 7

|  | Comp. Ex. 5 | Ex. 24 | Ex. 25 | Ex. 26 |
|---|---|---|---|---|
| Gum A (g) | 100 | 100 | 100 | 100 |
| Ca(OH)$_2$ (g) | 6 | 6 | 6 | 6 |
| MgO (g) | 3 | 3 | 3 | 3 |
| Carbon Black (g) | 30 | 30 | 30 | 30 |
| Onium A (mmhr) | 1.5 | 1.5 | 1.5 | 1.5 |
| Bisphenol A (mmhr) | 6.0 |  |  |  |
| Oxalate H (mmhr) |  | 6.0 |  |  |
| Oxalate I (mmhr) |  |  | 6.0 |  |
| Oxalate J (mmhr) |  |  |  | 6.0 |

TABLE 8

|  | Comp. Ex. 5 | Ex. 24 | Ex. 25 | Ex. 26 |
|---|---|---|---|---|
| Cure Temp. 150° C., 60 minutes |  |  |  |  |
| Minimum Torque (in-lb) (J) | 1.87 (0.211) | 1.81 (0.204) | 1.67 (0.188) | 1.86 (0.209) |
| Maximum Torque, (in-lb) (J) | 21.18 (2.39) | 24.68 (2.78) | 30.55 (3.44) | 17.43 (1.97) |
| TS$_2$ (minutes) | 1.38 | 22.31 | 46.09 | 13.24 |
| T50 (minutes) | 2.22 | 31.96 | 58.3 | 14.91 |
| T90 (minutes) | 3.72 | 45.97 | 74.68 | 19.85 |

TABLE 8-continued

| | Comp. Ex. 5 | Ex. 24 | Ex. 25 | Ex. 26 |
|---|---|---|---|---|
| MDR 177° C., 12 minutes | | | | |
| Minimum Torque (in-lb) (J) | 1.32 (0.149) | 1.08 (0.122) | 0.95 (0.107) | 1.18 (0.133) |
| Maximum Torque (in-lb) (J) | 18.59 (2.10) | 21.14 (2.39) | 26.72 (3.01) | 15.68 (1.76) |
| $TS_2$ (minutes) | .53 | 7.38 | 7.79 | 3.43 |
| T50 (minutes) | 0.71 | 9.57 | 10.44 | 4.16 |
| T90 (minutes) | 1.13 | 13.64 | 14.07 | 6.95 |
| MDR 200° C., 6 minutes | | | | |
| Minimum Torque (in-lb) (J) | 1.42 (0.160) | 0.75 (0.084) | 0.65 (0.073) | .82 (0.093) |
| Maximum Torque (in-lb) (J) | 17.05 (1.92) | 19.57 (2.21) | 24.54 (2.77) | 13.7 (1.545) |
| $TS_2$ (minutes) | 0.32 | 2.05 | 2.22 | 1.49 |
| T50 (minutes) | 0.40 | 2.81 | 3.29 | 1.91 |
| T90 (minutes) | 0.60 | 4.19 | 4.54 | 4.21 |

TABLE 9

| Sample | Comp. Ex. 5 | Ex. 24 | Ex. 25 | Ex. 26 |
|---|---|---|---|---|
| Tensile, MPa | 13.0 | 14.6 | 13.7 | 12.8 |
| Elongation, percent | 190 | 184 | 174 | 299 |
| Modulus, MPa | 5.53 | 5.51 | 5.66 | 3.05 |
| Shore A | 76 | 72 | 76 | 70 |
| Compression Set, percent | 30.2 | 26.8 | 26 | 47.8 |

Various modifications and alterations of this invention will become apparent to those skilled in the art without departing from the scope and spirit of the present invention, and it should be understood that this invention is not to be unduly limited to the illustrative embodiments set forth hereinabove.

What is claimed is:

1. A curable fluoropolymer composition comprising a mixture of:
   (a) fluorine-containing polymer or blend of fluorine-containing polymers each comprising interpolymerized units derived from one or more fluorine-containing ethylenically unsaturated monomers;
   (b) organo-onium compound; and
   (c) alkyl or aryl oxalate-blocked compound as a crosslinking agent.

2. The composition according to claim 1 wherein said oxalate blocked crosslinking agent is selected according to the formula:

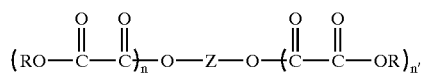

wherein
Z is an arylene or alkylarylene group;
R is an aryl group, substituted aryl group, arylalkyl group, substituted alkyl group, or an alkyl group; and
n or n' is 1 and each is independently selected as 0 or 1 with the proviso that when either n or n' is 0, its corresponding portion of the Z—O— moiety is terminated by hydrogen or is terminated by a metal or nonmetal cation.

3. The composition of claim 1 wherein said organo onium compound is selected from the group consisting of phosphonium, ammonium, sulfonium, acid-functional oniums, fluorinated oniums, and combinations thereof.

4. The composition of claim 2 wherein Z is a polyphenylene group.

5. The composition of claim 1 wherein the fluorine-containing polymer comprises a copolymer of vinylidine fluoride and at least one terminally ethylenically-unsaturated fluoromonomer other than vinylidine fluoride.

6. The composition of claim 1 wherein one or more of the fluorine-containing polymers comprise a copolymer of vinylidine fluoride and hexafluoropropene.

7. The composition of claim 1 wherein one or more of the fluorine-containing polymers comprise a terpolymer of vinylidine fluoride, hexafluoropropene, and tetrafluoroethylene.

8. The composition of claim 1 wherein said oxalate-blocked compound is an oligomer.

9. The composition of claim 1 wherein said one or more of the fluorine-containing polymers comprise a copolymer of vinylidine fluoride and hexafluoro propene or a terpolymer of vinylidine fluoride, hexafluoropropene, and tetrafluoroethylene, said organo-onium compound is selected from the group consisting of tributyl(2-methoxy) propylphosphonium chloride, carboxylethyltributylphosphonium chloride and combinations thereof, Z is a radical of bisphenol A or bisphenol AF, and R is phenyl, substituted phenyl, or an alkyl or substituted alkyl group having from 2 to 20 carbon atoms.

10. An article comprising a shaped elastomeric article comprising a cured composition comprising the reaction product of:
   (a) fluorine-containing polymer or blend of fluorine-containing polymers each comprising interpolymerized units derived from one or more fluorine-containing ethylenically unsaturated monomers;
   (b) organo-onium compound; and
   (c) alkyl or aryl oxalate-blocked compound as a crosslinking agent.

11. A method of making an article comprising the steps of:
   (1) forming an article from a curable fluoropolymer composition comprising a mixture of:
      (a) fluorine-containing polymer or blend of fluorine-containing polymers each comprising interpolymerized units derived from one or more fluorine-containing ethylenically unsaturated monomers,
      (b) organo-onium compound, and
      (c) alkyl or aryl oxalate-blocked compound as a crosslinking agent; and
   (2) curing said fluoropolymer composition.

12. The method of claim 11 wherein said fluoropolymer composition is cured by heating said composition at a temperature of about 95 to about 230° C. for a sufficient time to crosslink said fluoropolymer.

13. A method of curing a fluoropolymer comprising the steps of:
   (a) mixing organo-onium compound and alkyl or aryl oxalate-blocked compound into said fluoropolymer to form a curable fluoropolymer composition, said onium and oxalate-blocked compounds present in a sufficient amount to crosslink said fluoroelatomer to the desired degree; and
   (b) heating the curable fluoropolymer composition at a temperature of about 95 to about 230° C. for a sufficient time to crosslink said fluoropolymer.

* * * * *

UNITED STATES PATENT AND TRADEMARK OFFICE
CERTIFICATE OF CORRECTION

PATENT NO.    : 6,562,911 B2
DATED         : May 13, 2003
INVENTOR(S)   : Jing, Naiyong It is certified that error appears in the above-identified patent and that said Letters Patent is hereby corrected as shown below:

Columns 13 and 14,
Between Tables 1 and 3, insert the entire attached Table 2 which was omitted from the issued patent.

TABLE 2

| Cure Temp. 150 °C, 60 minutes | Comp. Ex. 1 | Ex. 8 | Ex. 9 | Ex. 10 | Ex. 11 | Ex. 12 | Ex. 13 | Ex. 14 | Comp. Ex. 2 | Ex. 15 | Comp. Ex. 3 | Ex. 16 |
|---|---|---|---|---|---|---|---|---|---|---|---|---|
| Minimum Torque (in-lb) (J) | 1.17 (0.132) | 1.15 (0.130) | 1.45 (0.164) | 1.68 (0.190) | 1.29 (0.146) | 1.35 (0.152) | 1.81 (0.204) | 0.74 (0.083) | 1.88 (0.212) | 1.34 (0.151) | 4.74 (0.535) | 3.50 (0.395) |
| Maximum Torque, (in-lb) (J) | 19.9 (2.24) | 22.9 (2.58) | 24.0 (2.71) | 20.9 (2.36) | 24.3 (2.74) | 24.9 (2.81) | 25.8 (2.91) | 25.7 (2.90) | 25.0 (2.82) | 19.4 (2.19) | 24.2 (2.73) | 27.6 (3.12) |
| $TS_2$ (minutes) | 1.91 | 35.04 | 32.37 | 13.23 | 24.57 | 38.42 | 13.03 | 11.35 | 2.30 | 13.54 | 1.04 | 46.70 |
| T50 (minutes) | 2.45 | 42.69 | 42.96 | 16.13 | 27.73 | 45.29 | 20.97 | 13.88 | 3.34 | 17.18 | 2.09 | 61.58 |
| T90 (minutes) | 3.28 | 55.09 | 57.92 | 22.90 | 33.84 | 52.90 | 30.18 | 22.72 | 5.03 | 20.90 | 3.48 | 73.98 |
| MDR 177 °C, 12 minutes | Comp. Ex. 1 | Ex. 8 | Ex. 9 | Ex. 10 | Ex. 11 | Ex. 12 | Ex. 13 | Ex. 14 | Comp. Ex. 2 | Ex. 15 | Comp. Ex. 3 | Ex. 16 |
| Minimum Torque (in-lb) (J) | 0.70 (0.079) | 0.59 (0.067) | 0.92 (0.104) | 0.94 (0.106) | 0.73 (0.082) | 0.82 (0.092) | 1.07 (0.121) | 0.35 (0.040) | 1.31 (0.148) | 0.76 (0.086) | 4.04 (0.456) | 2.42 |
| Maximum Torque (in-lb) (J) | 19.6 (2.21) | 24.1 (2.72) | 23.7 (2.68) | 18.0 (2.04) | 23.6 (2.67) | 24.8 (2.80) | 22.9 (2.58) | 21.8 (2.47) | 22.6 (2.55) | 21.3 (2.40) | 21.9 (2.52) | 22.3 (2.47) |
| $TS_2$ (minutes) | 0.56 | 5.40 | 3.48 | 2.11 | 3.98 | 3.66 | 1.84 | 1.55 | 0.64 | 2.95 | 0.55 | 7.67 |
| T50 (minutes) | 0.66 | 7.12 | 4.98 | 2.74 | 4.88 | 5.28 | 2.87 | 2.19 | 0.80 | 3.93 | 0.75 | 9.84 |
| T90 (minutes) | 1.00 | 9.73 | 8.00 | 4.09 | 7.36 | 7.92 | 5.15 | 3.28 | 1.16 | 5.84 | 0.97 | 11.00 |

TABLE 2

| MDR 200 °C, 6 minutes | Comp. Ex. 1 | Ex. 8 | Ex. 9 | Ex. 10 | Ex. 11 | Ex. 12 | Ex. 13 | Ex. 14 | Comp. Ex. 2 | Ex. 15 | Comp. Ex. 3 | Ex. 16 |
|---|---|---|---|---|---|---|---|---|---|---|---|---|
| Minimum Torque (in-lb) (J) | 0.78 (0.089) | 0.35 (0.040) | 0.59 (0.067) | 0.56 (0.063) | 0.44 (0.050) | 0.52 (0.059) | 0.74 (0.084) | 0.24 (0.027) | 1.15 (0.13) | 0.48 (.054) | 3.99 (0.450) | 1.69 (0.191) |
| Maximum Torque (in-lb) (J) | 18.2 (2.06) | 23.3 (2.64) | 21.9 (2.47) | 16.3 (1.84) | 20.4 (2.30) | 22.1 (2.49) | 19.9 (2.25) | 23.2 (2.61) | 18.2 (2.05) | 17.7 (2.00) | 19.6 (2.21) | 22.4 (2.53) |
| $TS_2$ (minutes) | 0.33 | 1.70 | 1.64 | 1.60 | 1.44 | 1.77 | 0.94 | 0.65 | 0.35 | 1.15 | 0.33 | 2.18 |
| T50 (minutes) | 0.40 | 2.33 | 2.22 | 1.95 | 1.82 | 2.28 | 1.36 | 0.96 | 0.43 | 1.48 | 0.42 | 2.93 |
| T90 (minutes) | 0.50 | 3.45 | 3.40 | 2.54 | 2.51 | 3.45 | 1.88 | 2.03 | 0.51 | 1.88 | 0.50 | 3.76 |

Column 15,
Lines 45 and 46, delete "J=50" and insert in place thereof -- J~50 --.

UNITED STATES PATENT AND TRADEMARK OFFICE
CERTIFICATE OF CORRECTION

PATENT NO.   : 6,562,911 B2
DATED        : May 13, 2003
INVENTOR(S)  : Jing, Naiyong It is certified that error appears in the above-identified patent and that said Letters Patent is hereby corrected as shown below:

Column 18,
Line 61, delete "fluoroelatomer" and insert in place thereof -- fluoroelastomer --.

Signed and Sealed this

Twenty-second Day of March, 2005

JON W. DUDAS
*Director of the United States Patent and Trademark Office*